(12) United States Patent
Kang et al.

(10) Patent No.: US 12,084,342 B2
(45) Date of Patent: Sep. 10, 2024

(54) METHOD FOR FORMING MICRO PATTERN ON SURFACE OF WIRE

(71) Applicant: Kookmin University Industry Academy Cooperation Foundation, Seoul (KR)

(72) Inventors: Bongchul Kang, Seoul (KR); Sihyung Lim, Seoul (KR)

(73) Assignee: Kookmin University Industry Academy Cooperation Foundation, Seoul (KR)

(*) Notice: Subject to any disclaimer, the term of this patent is extended or adjusted under 35 U.S.C. 154(b) by 555 days.

(21) Appl. No.: 17/224,379

(22) Filed: Apr. 7, 2021

(65) Prior Publication Data

US 2021/0403319 A1 Dec. 30, 2021

(30) Foreign Application Priority Data

Jun. 24, 2020 (KR) .................. 10-2020-0076900

(51) Int. Cl.
*B81C 1/00* (2006.01)
*A61B 5/026* (2006.01)
(Continued)

(52) U.S. Cl.
CPC .......... *B81C 1/00111* (2013.01); *A61B 5/026* (2013.01); *B22F 7/08* (2013.01);
(Continued)

(58) Field of Classification Search
CPC ......... B81C 1/00111; B81C 2201/0149; B81C 1/00166; B81C 2201/0188; A61B 5/026;
(Continued)

(56) References Cited

U.S. PATENT DOCUMENTS

2012/0015112 A1* 1/2012 Yang ............... H05K 3/105
427/555

FOREIGN PATENT DOCUMENTS

JP           4467633 B2 *  5/2010  ............ B23K 26/06
KR   10-2013-0081870 A    7/2013
(Continued)

OTHER PUBLICATIONS

JP-4467633-B2 Translation (Year: 2010).*
(Continued)

*Primary Examiner* — Brian D Walck
*Assistant Examiner* — Danielle Carda
(74) *Attorney, Agent, or Firm* — Sughrue Mion, PLLC

(57) ABSTRACT

A method for producing a micro-pattern on surface of a wire is disclosed. The method includes a step of applying a nanoparticle solution to the wire to form a nanoparticle solution layer on the surface of the wire; and a step of irradiating the nanoparticle solution layer with a Bessel beam laser to induce sintering of nanoparticles, thereby forming a micro-pattern on the surface of the wire. It is possible to form a microelectrode pattern on a level of several to tens of micrometers on the surface of a micro-wire having a diameter on a scale of several tens to several hundreds of micrometers. Since a laser optical system with a long depth of focus is used, a micro-pattern with a uniform thickness can be formed on surface of a wire having a curvature in a simple.

17 Claims, 18 Drawing Sheets

(51) Int. Cl.
 *B22F 7/08* (2006.01)
 *B81B 1/00* (2006.01)
(52) U.S. Cl.
 CPC ........ *B81B 1/008* (2013.01); *B81B 2201/055* (2013.01); *B81B 2203/0361* (2013.01); *B81C 2201/0149* (2013.01)

(58) Field of Classification Search
 CPC .. B22F 7/08; B22F 10/20; B22F 12/44; B22F 2999/00; B22F 3/24; B22F 12/41; B22F 2003/242; B22F 1/0545; B81B 1/008; B81B 2201/055; B81B 2203/0361; B81B 2201/0278; B81B 2201/0292; B81B 2203/04; B81B 2207/07; C23C 24/04; C23C 26/00; Y02P 10/25; B23K 26/359; B23K 26/16; B23K 26/364
 USPC .......................................................... 419/23
 See application file for complete search history.

(56) References Cited

FOREIGN PATENT DOCUMENTS

| KR | 20130081870 A | * | 7/2013 | ............. B82B 1/005 |
| KR | 10-2013-0092857 A | | 8/2013 | |
| KR | 10-1357179 B1 | | 2/2014 | |
| KR | 10-2019-0139213 A | | 12/2019 | |

OTHER PUBLICATIONS

KR-20130081870-A Translation (Year: 2013).*
Chem Europe Encyclopedia, Substrate (materials science) (Year: 2023).*
Lin Li et al., "Laser nano-manufacturing-State of the art and challenges", CIRP annals—Manufacturing Technology 60, 2011, pp. 735-755.
Jaeho Park et al., "Biopsy Needle Integrated with Electrical Impedance Sensing Microelectrode Array towards Real-time Needle Guidance and Tissue Discrimination", Scientific Reports, published online Jan. 10, 2018, vol. 8, No. 264, 20pages.

* cited by examiner

METHOD FOR FORMING MICRO PATTERN ON SURFACE OF WIRE

CROSS REFERENCE TO RELATED APPLICATIONS

This application claims priority and benefit under 35 U.S.C. § 119 based on Korean Patent Application No. 10-2020-0076900 filed Jun. 24, 2020, of which the content is incorporated by reference herein.

FIELD OF THE DISCLOSURE

The present invention relates to a method for preparing a micro-pattern on the surface of a wire, and more particularly, to a method for forming a micro-pattern on the surface of a wire having a curvature using laser irradiation.

BACKGROUND

A wire refers to a metal thread or a thread of various materials connected for a length, and includes various types depending on thickness and applications. Round wires whose cross-section is circular are used most commonly out of various wires according to thickness, shape, and applications, and these wires are used for various purposes in diverse fields such as medical, electronic, mechanical, etc.

Recently, attempts have been actively made to utilize wires in electronic devices due to the compactness of electronic devices and the popularity of flexible electronic devices such as wearable devices, and in particular, various applications are being developed for connecting wiring to micro-wires having a diameter on a level of micrometers.

In this regard, a technique has been proposed for penetrating a wire in the form of a micro-needle into the body of a human or animal and for collecting bodily information such as a blood flow rate, body temperature, etc., to be utilized in diagnosing a disease. To this end, an ultra-precision technique for forming microelectrode wiring on the surface of a wire is required beyond the conventional method of using the wire itself as an electrode or wiring.

Jaeho Park et al., "Biopsy Needle Integrated with Electrical Impedance Sensing Microelectrode Array towards Realtime Needle Guidance and Tissue Discrimination," *SCIENTIFIC REPORTS*, (2018) 8: 264 introduces a biopsy needle with an electrical impedance sensor array based on microelectrodes. In order to construct an electrode array on a micro-needle, Jaeho Park et al. describes a process of first insulating the needle, followed by applying a PSA coating, attaching a pre-produced electrode pattern, and then insulating again. However, the method of attaching the electrode pattern prepared in advance to the wire as described above had issues that the durability of the electrode pattern was poor, the diameter of a fabricated wire became larger than that of the original wire because an adhesive coating layer was absolutely necessary, and there was a limit to forming a precise pattern on a scale of several microns to tens of microns.

Therefore, there is a need for a technique of forming micro-patterns directly on the surface of a wire instead of a method of attaching a pre-produced electrode pattern; however, a technique that allows a micro-pattern to be formed directly on the surface of a wire has not yet been developed because of the surface curvature of a wire.

For example, Korean Laid-open Patent Publication No. 10-2019-0139213 introduces a technique for forming a texture on the surface of a wire, but this is nothing but a technique of coating the entire surface of the wire and then performing a surface treatment to form a repetitive surface texture, and is far from the technique of forming a microelectrode pattern on the surface of a wire.

Accordingly, if it is possible to form a micro-pattern directly on the surface of a micro-wire, it is expected to have high utilization in various special applications that have been difficult to implement so far due to technical limitations, such as micro-sensors to be inserted into blood vessels of the human body.

SUMMARY OF THE INVENTION

Technical Objects

The present invention is designed to solve the problems of the prior art as described above, and it is an object of the present invention to provide a method for forming a micro-pattern on the surface of a wire having a curvature in a simple and fast process.

It is another object of the present invention to provide a wire produced by the method described above and having a micro-pattern formed on the surface thereof.

Technical Solution

In order to achieve the objects as described above, the present invention provides a method for forming a micro-pattern on a surface of a wire, comprising: a step of applying a nanoparticle solution to the wire to form a nanoparticle solution layer on the surface of the wire; and a step of irradiating the nanoparticle solution layer with a Bessel beam laser to induce sintering of nanoparticles, thereby forming a micro-pattern on the surface of the wire.

The method of the present invention may further comprise a step of fixing both ends of the wire, before the step of applying the nanoparticle solution to the wire.

In addition, the method of the present invention may further comprise a step of fixing both ends of the wire, after the step of applying the nanoparticle solution to the wire.

Moreover, the method of the present invention may, after the step of irradiating the nanoparticle solution layer with the Bessel beam laser, repeating: a step of rotating the wire so that an area having no micro-pattern formed on the wire is positioned at a focal point of the Bessel beam laser; and a step of irradiating the nanoparticle solution layer of the area with the Bessel beam laser to induce sintering of the nanoparticles, thereby forming a micro-pattern on the surface of the wire.

The method of the present invention may further comprise a step of removing a residual nanoparticle solution, after the step of irradiating the nanoparticle solution layer with the Bessel beam laser.

In the method of the present invention, application of the nanoparticle solution may be performed by dip coating.

In the method of the present invention, application of the nanoparticle solution may be performed by spray coating or inkjet coating.

In the method of the present invention, the wire may have a diameter of 1 μm to 10 mm.

In the method of the present invention, the nanoparticle solution may have a content of nanoparticles of 5 to 35% by weight.

In the method of the present invention, the nanoparticle solution may have a viscosity of 10 to 200 cP.

In the method of the present invention, the nanoparticles may be one or more selected from a group consisting of copper (Cu), aluminum (Al), chromium (Cr), nickel (Ni), gold (Au), silver (Ag), cobalt (Co), iron (Fe), palladium (Pd), platinum (Pt), titanium (Ti), zinc (Zn), and silica.

In the method of the present invention, the nanoparticle solution may be a solution in which the nanoparticles are dispersed or dissolved in one or more solvents selected from a group consisting of distilled water, deionized water, isopropanol, ethanol, methanol, butanol, propanol, glycol ether, acetone, toluene, dichloromethane, tetrahydrofuran (THF), and dimethylformamide.

In the method of the present invention, the nanoparticle solution layer may be applied with a thickness of 10 nm to 1 mm to the surface of the wire.

The method of the present invention may, with a position of the wire fixed, move a focal point of the Bessel beam laser to irradiate a predetermined area of the nanoparticle solution layer with the laser.

The method of the present invention may, with a position of the focal point of the Bessel beam laser fixed, move a position of the wire to irradiate a predetermined area of the nanoparticle solution layer with the laser.

In the method of the present invention, the laser may have a power of 1 to 10 W.

In the method of the present invention, the fixing the wire may be performed by pulling both ends so that a constant tension is maintained on the wire.

Further, the present invention provides a wire having a micro-pattern on a surface thereof, wherein the micro-pattern is formed by the method described above.

Moreover, the present invention provides a sensor comprising the wire described above.

In the present invention, the sensor may be a flow rate sensor or a temperature sensor for insertion into a body.

Effects of the Invention

According to the present invention, since it is possible to form a microelectrode pattern on a level of several to tens of micrometers on the surface of a micro-wire having a diameter on a scale of several tens to several hundreds of micrometers, a microelectrode sensor that could not have been implemented by the method of rolling and attaching a pre-produced electrode pattern onto a wire can be manufactured.

In addition, since the method of the present invention utilizes a laser optical system with a long depth of focus, it is possible to form a micro-pattern with a uniform thickness on the surface of a wire having a curvature in a simple and fast process without fine-tuning the focus of the laser.

DETAILED DESCRIPTION OF THE PREFERRED EMBODIMENTS

Hereinafter, specific implementations of the present invention will be described in greater detail. Unless defined otherwise, all technical and scientific terms used herein have the same meaning as commonly understood by a person skilled in the art to which the present invention pertains. In general, the nomenclature used herein is well known and commonly used in the art.

The present invention relates to a method for forming a micro-pattern on the surface of a wire, and the micro-pattern can be formed directly on the surface of the wire having a diameter on a scale of several tens to several hundreds of micrometers in accordance with the present invention.

A method of the present invention may comprise forming a nanoparticle solution layer on a surface of a wire by applying a nanoparticle solution to the wire; and forming a micro-pattern on the surface of the wire by inducing sintering of nanoparticles by irradiating the nanoparticle solution layer with a laser.

According to a preferred embodiment of the present invention, the method of the present invention may further comprise fixing the wire, after forming the nanoparticle solution layer.

According to another preferred embodiment of the present invention, the method of the present invention may further comprise fixing the wire, before forming the nanoparticle solution layer.

According to a preferred embodiment of the present invention, the method of the present invention may further comprise removing a residual nanoparticle solution, after forming the micro-pattern on the surface of the wire.

Figure 1:
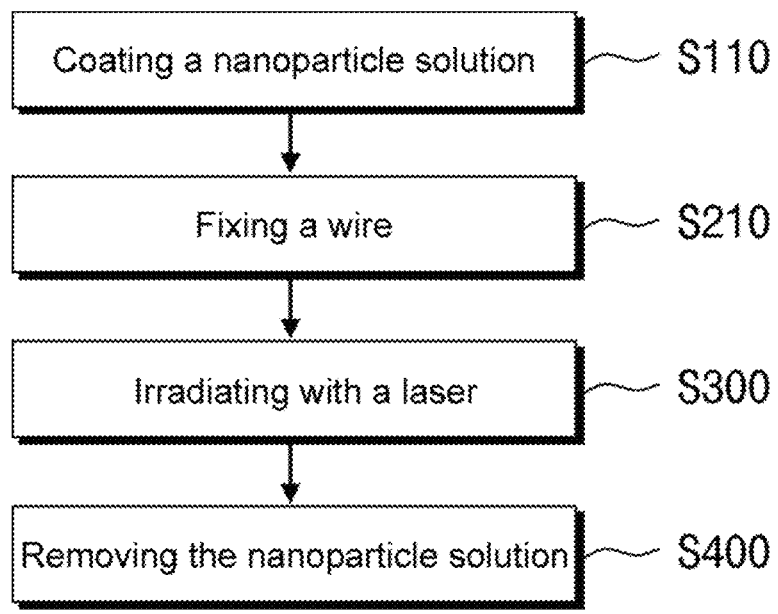
FIG. 1 shows a process flow chart of a method for forming a micro-pattern on a surface of a wire in accordance with a preferred embodiment of the present invention.
Figure 2:
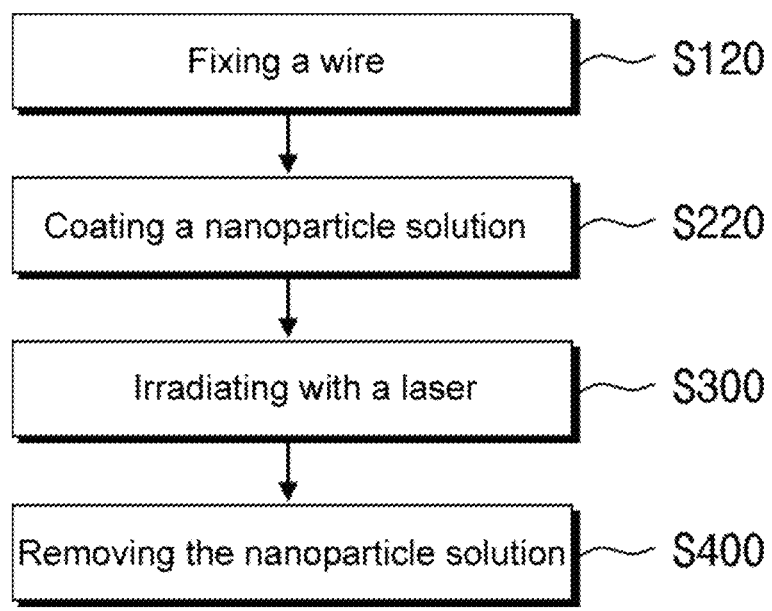
FIG. 2 shows a process flow chart of a method for forming a micro-pattern on a surface of a wire in accordance with another preferred embodiment of the present invention.

FIGS. 1 and 2 show a process diagram of a method for forming a micro-pattern on a surface of a wire in accordance with a preferred embodiment of the present invention.

As shown in the process diagram of FIG. 1, in one embodiment of the present invention, the method of the present invention may comprise coating a wire with a nanoparticle solution (S110), fixing the wire (S210), irradiating the nanoparticle solution layer with a laser to form a micro-pattern (S300), and removing a residual nanoparticle solution (S400).

In addition, as in the process diagram shown in FIG. 2, in one embodiment of the present invention, the method of the present invention may comprise fixing a wire (S120), coating the wire with a nanoparticle solution (S220), irradiating the nanoparticle solution layer with a laser to form a micro-pattern (S300), and removing a residual nanoparticle solution (S400).

The material of the wire that can be used in the present invention may use polymers such as polyethylene (PE), polyethylene terephthalate (PET), and polyvinyl chloride (PVC); metals such as aluminum (Al), iron (Fe), gold (Au), silver (Ag), copper (Cu), titanium (Ti), and zinc (Zn), or oxides thereof, for example, $TiO_2$, ZnO; ceramics such as silicon carbide, silicon nitride, alumina, zirconia, and barium titanate; carbon materials; or, composites thereof.

In addition, the wire may include a wire made by layering the materials described above or having the surface of the wire coated with the materials described above.

For the wire, it is desirable to use a round wire having a circular cross-section that is generally used, but the invention is not limited thereto, and it is also possible to use a wire having a square or pentagonal cross-section rather than a circular cross-section.

The wire that can be used in the present invention may have a diameter of 1 μm to 10 mm. Since the micro-pattern formed by the process of the present invention has a resolution of 1 μm or less, it is possible to form the micro-pattern even on the surface of a wire having a diameter of about 1 μm. Further, although there is no technical limitation in forming the micro-pattern by applying the method of the present invention even if the diameter of the wire is larger, there are restrictions on its use in various applications if the diameter is excessively large.

The method for forming a micro-pattern on the surface of a wire of the present invention comprises applying a nanoparticle solution to the wire to form a nanoparticle solution layer (S110, S220).

The nanoparticle solution refers to a solution in which nanoparticles having various sizes ranging from several nanometers (nm) to several hundreds of micrometers (m) are dissolved or dispersed in a solvent. Although the size of the nanoparticles may be applied differently depending on the type of material to be coated, it is preferable to have an average particle diameter of 10 to 500 nm, and more preferable to have an average particle diameter of 50 to 100 nm in consideration of the uniformity of the coating.

The nanoparticles are the ones made by powdering the material for forming the micro-pattern on the wire, and may preferably be metal nanoparticles mainly used as an electrode material. For example, conductive materials such as copper (Cu), aluminum (Al), iron (Fe) may be used but are not particularly limited thereto, and metal nanoparticles such as platinum (Pt), palladium (Pd), chromium (Cr), nickel (Ni), gold (Au), silver (Ag), cobalt (Co), titanium (Ti), and zinc (Zn), or a mixture of these may be used.

In addition, the nanoparticles are not limited to metal nanoparticles, and non-metal nanoparticles such as silica nanoparticles may also be used.

For the solvent that can be used in the present invention, an inorganic solvent such as distilled water or deionized water, or an organic solvent such as isopropanol, ethanol, methanol, butanol, propanol, glycol ether, acetone, toluene, dichloromethane, tetrahydrofuran (THF), dimethylformamide, etc. may be used.

The nanoparticles may be present in a dispersed or dissolved state in a solvent, and they may be present in the form of ions when the nanoparticles are dissolved in a solvent.

In the nanoparticle solution, the content of nanoparticles is preferably 5 to 35% by weight. If the content of the nanoparticles is less than 5% by weight, it is difficult to form a micro-pattern, and if over 35% by weight, the coating of the micro-pattern may be uneven or it may take an excessive time for growth and sintering.

In addition, it is preferable for the nanoparticle solution to have a viscosity of 10 to 200 cP. If the viscosity of the nanoparticle solution is too low, the coating will not be well maintained on the wire, making the process difficult, and if the viscosity is too high, the workability will be poor.

The nanoparticle solution layer is preferably applied with a thickness of 10 nm to 1 mm.

The method for applying (coating) the nanoparticle solution to the wire may use a known process capable of uniformly applying the solution to the wire, and may use dip coating, spray coating, inkjet coating, and the like, for example.

In the coating process, a step of drying the nanoparticle solution may be performed as necessary. The solvent of the nanoparticle solution may be evaporated through the step of drying, and the coating and drying of the nanoparticle solution may also be repeated several times.

In a preferred embodiment of the present invention, the order of the step of fixing the wire (S210, S120) may be determined according to the process of applying the nanoparticle solution layer to the surface of the wire. In the case of dip coating in which the wire is immersed in the nanoparticle solution and then is taken out, it is preferable to fix the wire after coating the nanoparticle solution, and in the case of spray coating or inkjet coating, it is more preferable to perform coating after fixing the wire. For example, the wire may be first fixed and then the nanoparticle solution may be coated by operating it to pass over a nozzle.

In the present invention, "fixing" refers to pulling both ends of an area of the wire on which the micro-pattern is to be formed to maintain a constant tension, so that the shape of the wire does not change, such as bending, during the coating process. The wire fixed in this way can be moved under such tension for laser irradiation to be described later, and it does not mean that the wire is fixed in a particular location.

The "ends" of the wire refer to both ends of the area on which the micro-pattern is to be formed, and they are not necessarily limited to the ends of the entire length of the wire.

After coating the wire with the nanoparticle solution layer and fixing the wire (or in reverse order), a laser is irradiated onto the nanoparticle solution layer to induce sintering of the nanoparticles, thereby allowing the micro-pattern to be formed on the wire (S300).

According to the prior art, in order to form a micro-pattern on a wire, a method of forming a micro-pattern on a release paper and then rolling and attaching it onto the surface of the wire was used. In the case of using such a method, there were problems that it was difficult to form a detailed pattern, the process was complicated, and the binding force of the micro-pattern was weak. Until now, a technique for directly forming a micro-pattern on the surface of a wire has not been studied.

In general, in order to obtain a thin film uniformly sintered on a three-dimensional substrate using a laser, a sintering process must be carried out with the exact focus on the irregular surface of the substrate, but focusing the laser on the irregular substrate of a three-dimensional shape involves considerable technical difficulty. Since the length of a laser beam capable of sintering stably is within several times the focal point, it is necessary to move the substrate or the focal position in real-time so that the focal point of the laser is accurately positioned on the sintering site of the substrate. In this case, an additional precision system for positioning is required, and process difficulty and cost increase dramatically.

In the present invention, a micro-pattern was formed on the surface of a wire having a curvature by using a modified beam having a long focal point using an optical system. Specifically, an attempt was made to produce a micro-pattern by constructing an optical system having a long depth of focus using a Bessel beam in the present invention.

Figure 3A:
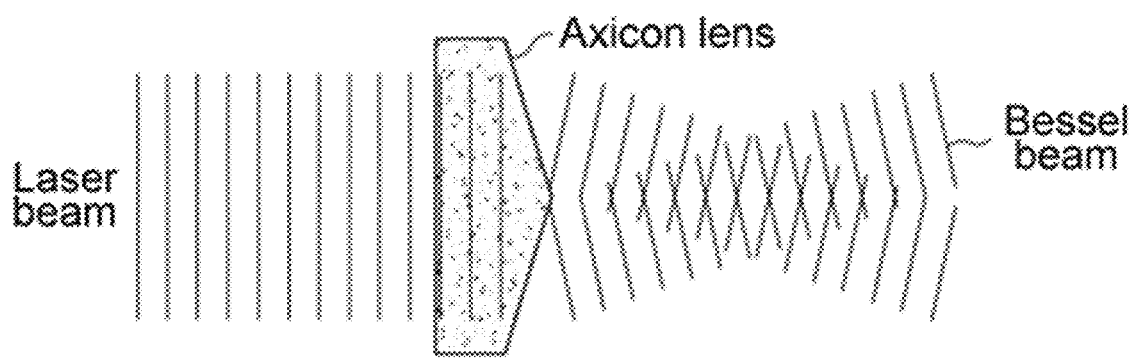
FIG. 3a is a view illustrating the principle of a Bessel beam.
Figure 3B:
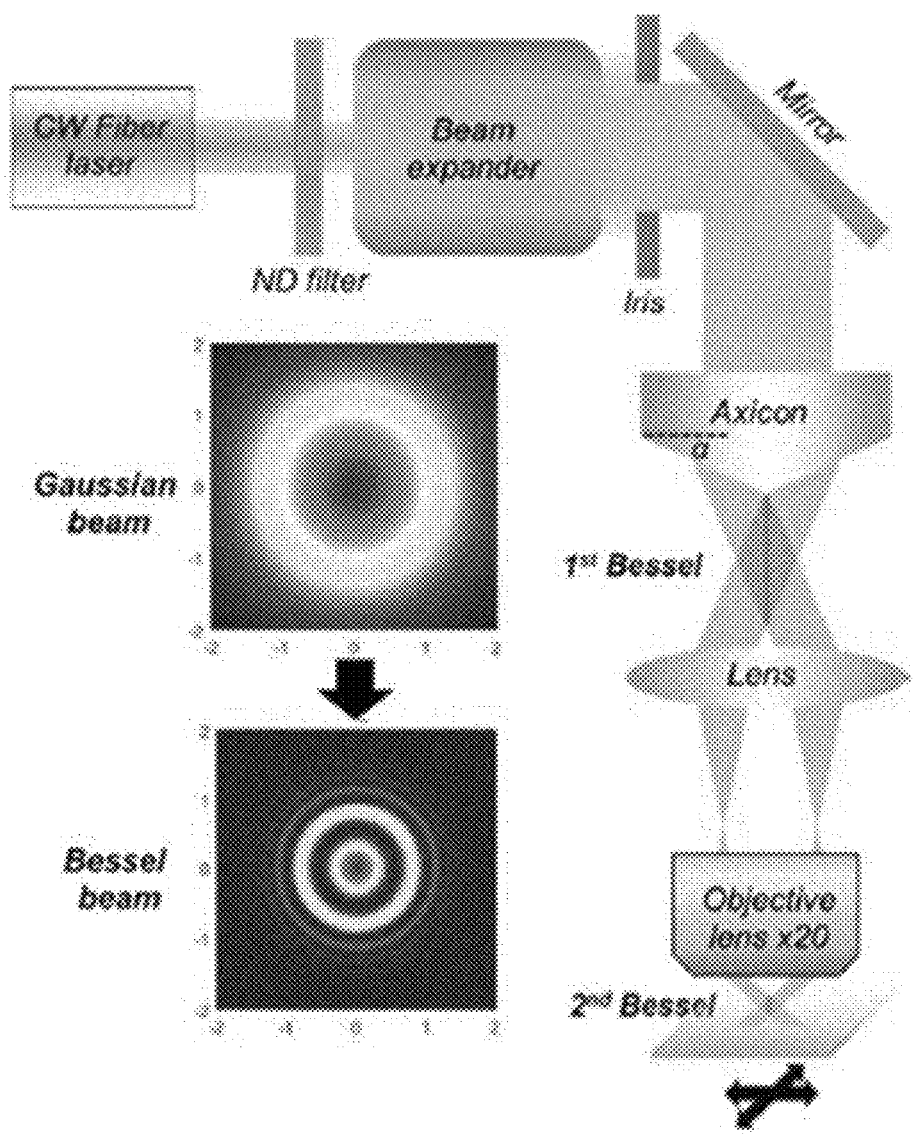
FIG. 3b shows a conceptual diagram of an optical system for implementing a Bessel beam.

FIGS. 3a and 3b are conceptual diagrams schematically showing (a) the principle of a Bessel beam and (b) an optical system for implementing the Bessel beam. A laser beam whose cross-sectional profile is a Gaussian shape can be converted into a Bessel beam using an Axicon Lens. Here, a case of using an axicon lens is described as an example, but the present invention is not necessarily limited thereto, and not only the axicon lens but also an annular ring or an annular slit may also be used. The Gaussian shape, which is the basic beam profile of a laser, consumes a lot of energy and makes it difficult to focus a beam close to the wavelength of light, resulting in difficulty to form a micro-pattern close to the wavelength of light. However, since the Bessel beam focuses on a small area, reduces energy consumption, and increases the concentration to thereby reduce the focal size of the beam, it can form a pattern of the size of the wavelength of light, can focus by using interference, and can form a micro-pattern on the surface of the wire by having a long depth of focus.

Further, when a circular beam is converted into a Bessel beam using an axicon lens and passed through a beam expander, the size of the beam changes, and at this time, the size of the beam can be freely changed by adjusting the beam expander. If the size of the Bessel beam changes freely, the focus area changes in response to the adjustment of the expander, and this makes it possible to overcome the limited depth of focus and to pattern the surface of the wire having a curvature.

Figure 4:
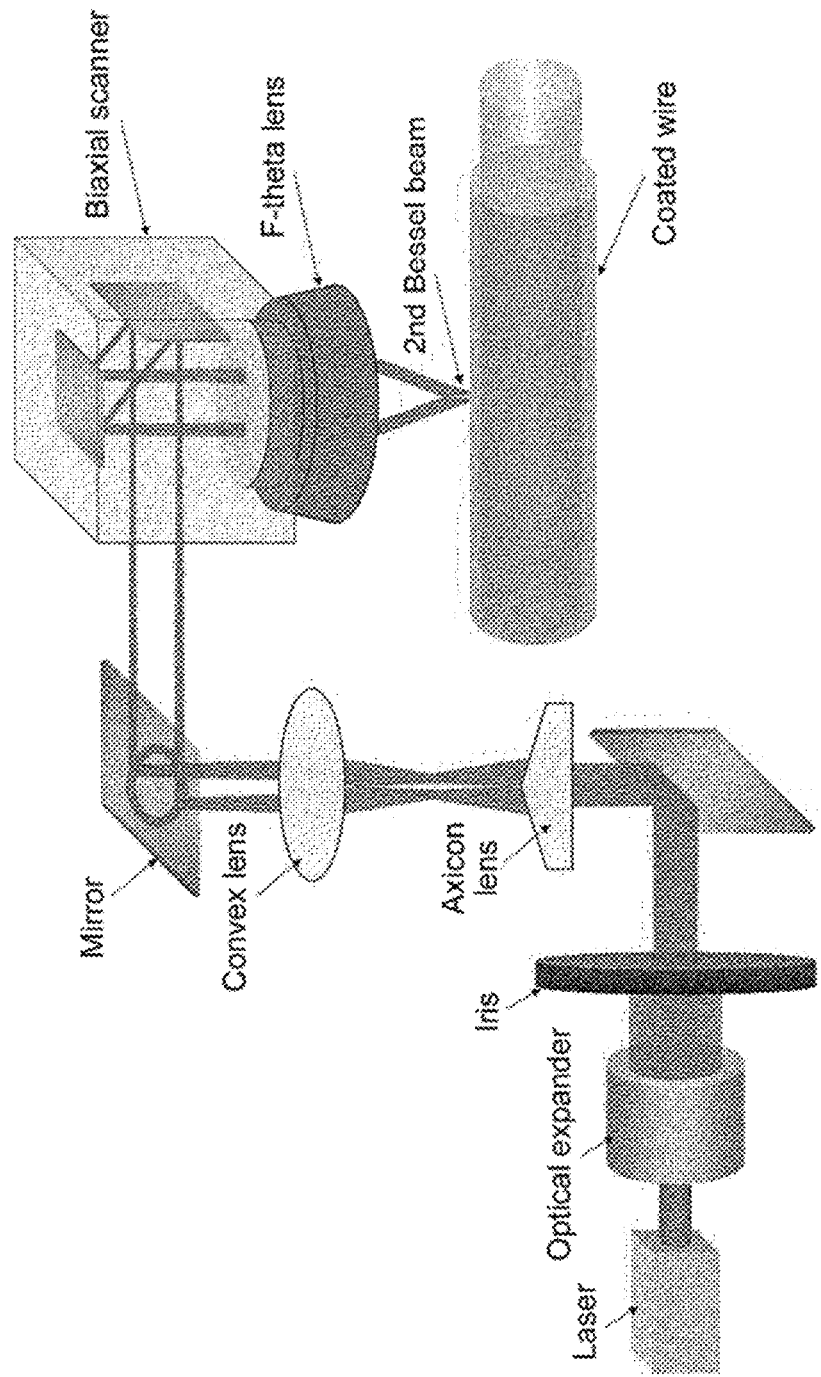
FIG. 4 illustrates the configuration of an example optical system of the present invention using a biaxial scanner and an F-theta lens.

FIG. 4 illustrates the configuration of an example optical system of the present invention, showing a configuration for implementing a Bessel beam using a biaxial scanner and an F-theta lens. The laser that has passed through an optical expander and an iris passes through an axicon lens to change its shape from a Gaussian beam to a Bessel beam, thereby forming a primary Bessel beam. Then, it passes through a convex lens to form a beam so as not to diverge, is made to be controllable to a desired shape through a biaxial scanner, and is passed through the F-theta lens to form a secondary Bessel beam. The formed secondary Bessel beam and the biaxial scanner may be used to sinter the metal nanoparticles applied to the surface of the wire, thereby forming a micro-pattern.

Figure 5:
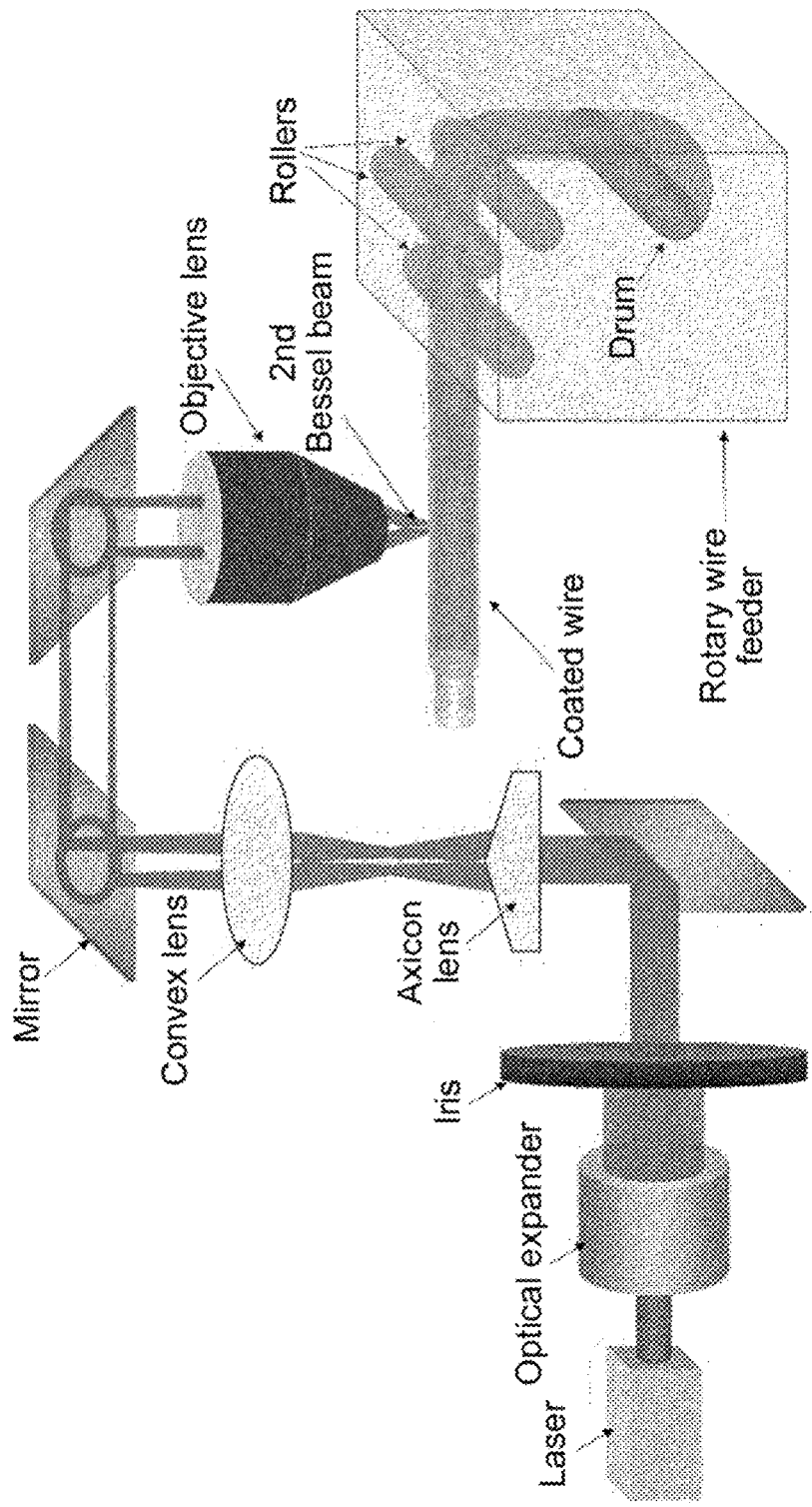
FIG. 5 illustrates the configuration of another example optical system of the present invention using an objective lens.

FIG. 5 illustrates the configuration of another example optical system of the present invention. In FIG. 5, the laser that has passed through an optical expander and an iris passes through an axicon lens to change its shape from a Gaussian beam to a Bessel beam, thereby forming a primary Bessel beam. Then, it passes through a convex lens to form a beam so as not to diverge, and passes through an objective lens to form a secondary Bessel beam. A rotary wire feeder may be used to control the movement of the wire, and the secondary Bessel beam may be irradiated to sinter the metal nanoparticles on the surface of the wire, thereby forming a micro-pattern.

The optical systems described with FIGS. 4 and 5 are illustrative and are not intended to limit the scope of the present invention, and various optical systems may be configured and used within a scope for implementing a Bessel beam laser having a long depth of focus.

When the nanoparticle solution layer coated on the wire is irradiated with a laser beam, the size of the nanoparticles increases as they are heated and grow, causing them to be bonded to each other and sintered. At this time, the sintering of the nanoparticles can form a pattern with a resolution on a level of about 1 µm if the focal size of the laser beam is adjusted to 1 µm. Accordingly, it is possible to precisely form a micro-pattern on the surface of the wire.

Figure 6:
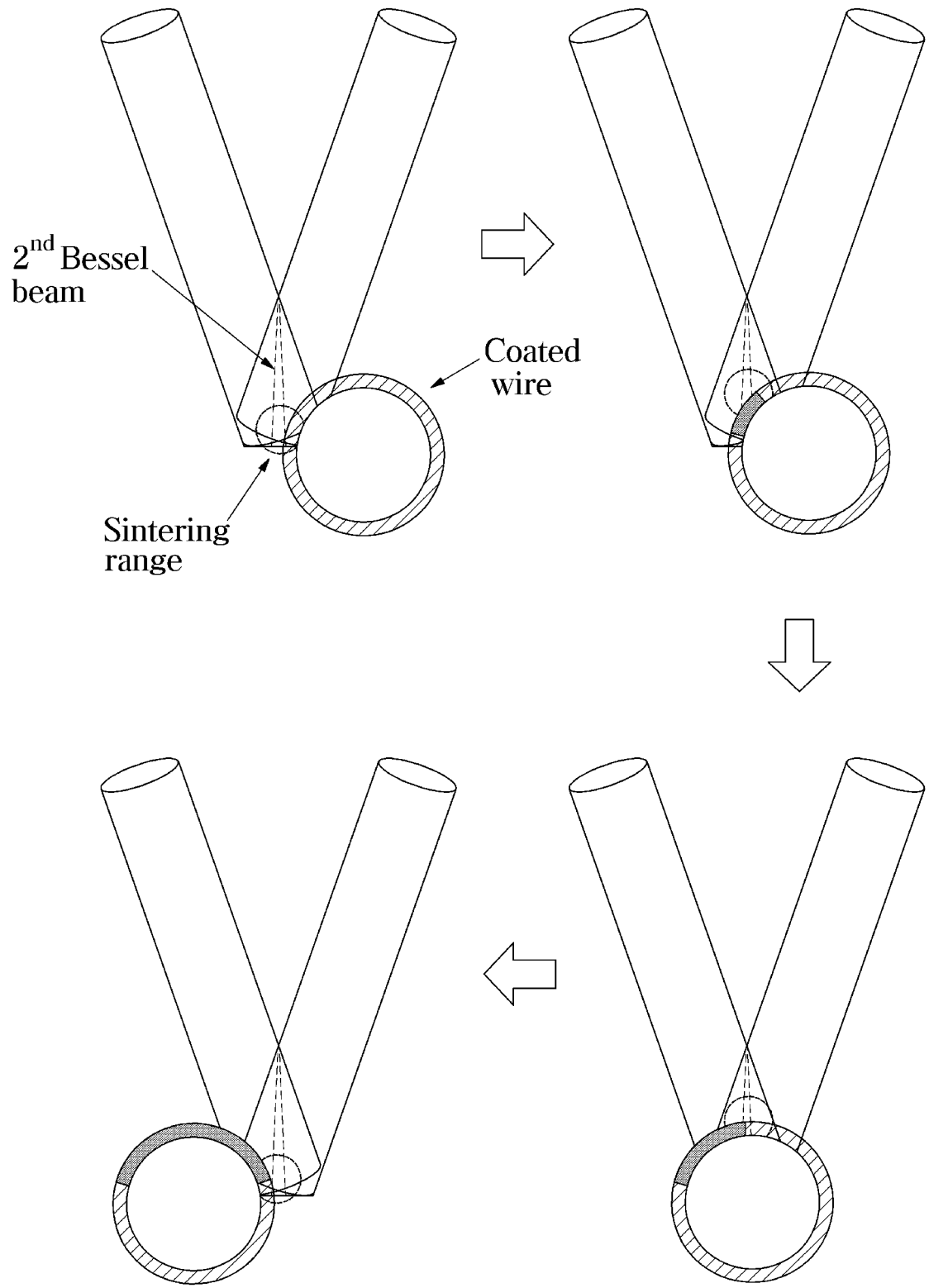
FIG. 6 illustrates a process of sintering nanoparticles by applying the focal point of a Bessel beam onto a nanoparticle solution applied to a surface of a wire.

FIG. 6 illustrates a process of sintering nanoparticles by applying the focal point of a Bessel beam onto a nanoparticle solution applied to a surface of a wire. Since the Bessel beam has a long depth of focus, the nanoparticle solution applied to the top and side surfaces of the wire can be heated and sintered without adjusting the height of the focal point. Therefore, according to the method of the present invention, a micro-pattern can be formed up to a central angle of 180°, preferably a central angle of 160° based on the cross-section of the wire in one operation without rotating the wire. This means that an area of approximately 40 to 50% based on the entire 360° can be processed in one operation.

The central angle at which the surface of the wire is sintered (hereinafter, a sintered angle) gradually decreases as the diameter of the wire increases.

Figure 7:
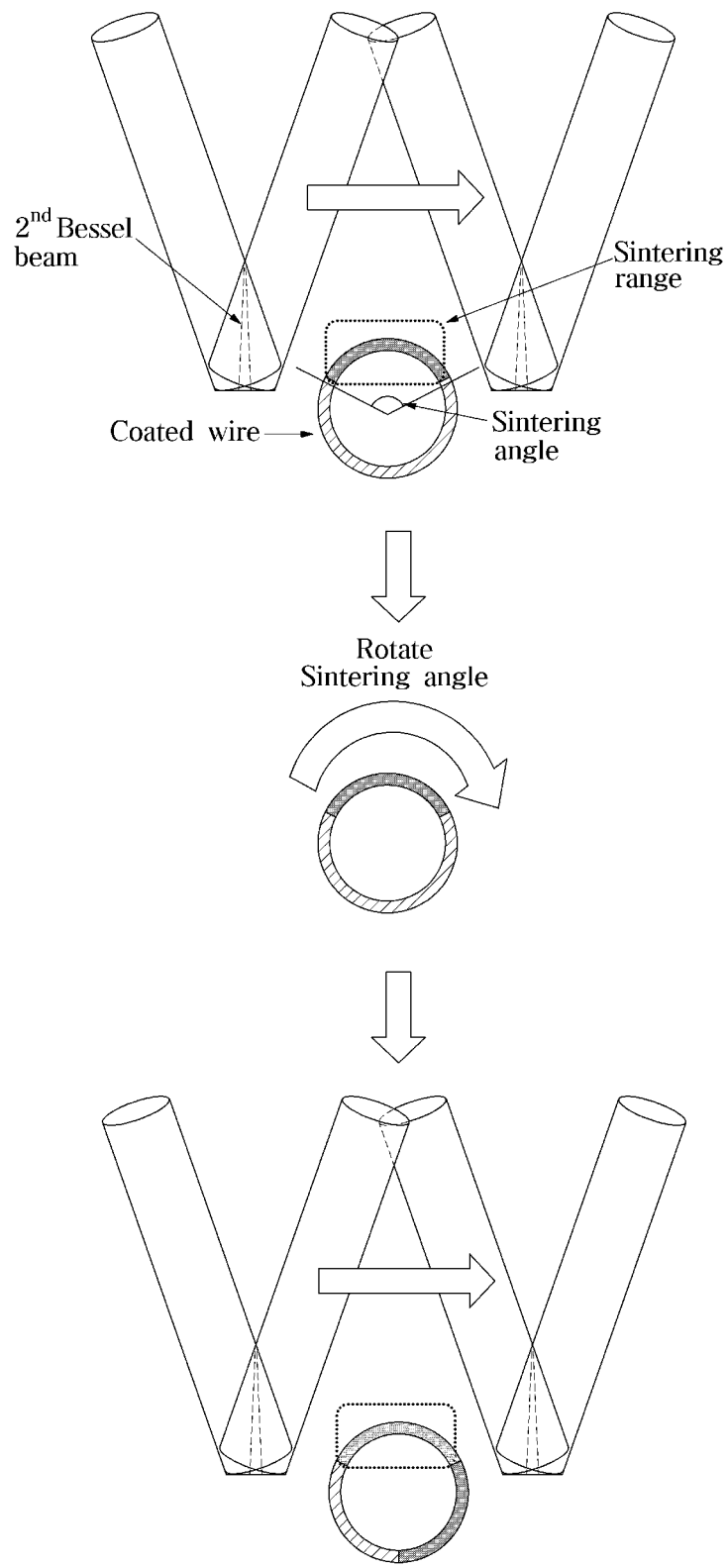
FIG. 7 illustrates a process of forming a micro-pattern on an entire surface of a wire.

In addition, if a micro-pattern is to be formed on the entire surface of the wire as shown in FIG. 7, a micro-pattern may be first formed on the surface area of the wire where the sintering angle is 120° or more, and then a process of rotating the wire and forming the micro-pattern on the remaining area may be repeated to form the micro-pattern on the entire surface of the wire.

The wavelength of the laser that can be used in the present invention may be ultraviolet, visible, or infrared light, and the types of lasers may include, for example, a pulse laser of fs (femtoseconds) to ms (milliseconds), a continuous wave (CW) laser, a quasi-continuous wave (QCW) laser, and the like.

In the present invention, the laser irradiation may be configured to form a micro-pattern on a larger area and faster by processing line beams in parallel rather than in one device, or irradiating the line beams in multiple using an array lens or the like.

Further, since a sintered micro-pattern is formed only on the area to which the laser is irradiated, it is possible to form a pattern of a free shape by a method of moving the focal point of the laser. The method of moving the focal point of the laser may be, for example, moving the laser with the wire fixed, or moving the wire with the laser fixed. In this case, since the wire is placed upon a moving means, the wire may be moved by moving the moving means. In addition to the method of moving the laser or wire using the moving means in this way and irradiating the patterning area with the laser, a method of moving and irradiating the Bessel beam using a galvano scanner, and a method using a combination of these two methods may be used.

After moving the laser to the area for forming the micro-pattern in this way, the focus of the Bessel beam is adjusted, where the focus may be adjusted, for example, using an objective lens, a scanner, or the like. In addition, the process temperature, the scan rate of the laser beam, the power of the laser beam, the pulse width, the repetition rate, and the like, which may affect the area or thickness of the micro-pattern to be formed, may be adjusted.

In this case, the power of the laser beam is preferably 1 to 10 W. Irradiating with the laser beam of the above power range can heat the nanoparticles to 100 to 2000° C., causing the nanoparticles to be grown and sintered in a short time.

The process of the present invention can carry out patterning at a very high speed because it uses a laser beam. Specifically, the micro-pattern can be formed on the surface of the wire at a speed of 1 mm/s to 10 m/s, and preferably, the micro-pattern can be formed at a speed of about 3 m/s.

The depth of focus of the Bessel beam may be adjusted differently according to the configuration of the optical system, and a depth of focus of 100 μm or more can be implemented using a beam expander, and therefore, it is possible to form a micro-pattern resulting from the sintering of the nanoparticles by moving the focal point only horizontally without an operation of moving it up and down even on the curved surface of the wire.

The process of forming a micro-pattern of the present invention can form a micro-pattern by irradiating only a necessary area with a laser after coating a wider area of the entire surface of the wire with a nanoparticle solution layer without having to form the nanoparticle solution layer precisely only in the portion where the micro-pattern is to be formed on the surface of the wire. Therefore, a precise process is not required for coating the nanoparticle solution layer, and common coating processes such as dip coating, spray coating, and the like are sufficient.

Moreover, the method of the present invention may further comprise removing a residual nanoparticle solution (S400), after forming the micro-pattern on the wire. The process of removing or cleaning the nanoparticle solution may use a method of utilizing ultrasonic waves, spray, etc., or a method of utilizing a cleaning solution such as ethanol or acetone, but is not particularly limited thereto.

Figure 8A:
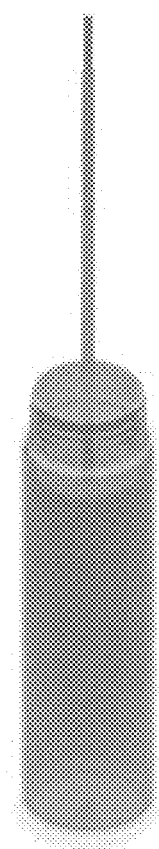
FIGS. 8a to 8c depict illustratively a process of forming a micro-pattern on a surface of a wire in accordance with a method of the present invention.
Figure 8B:
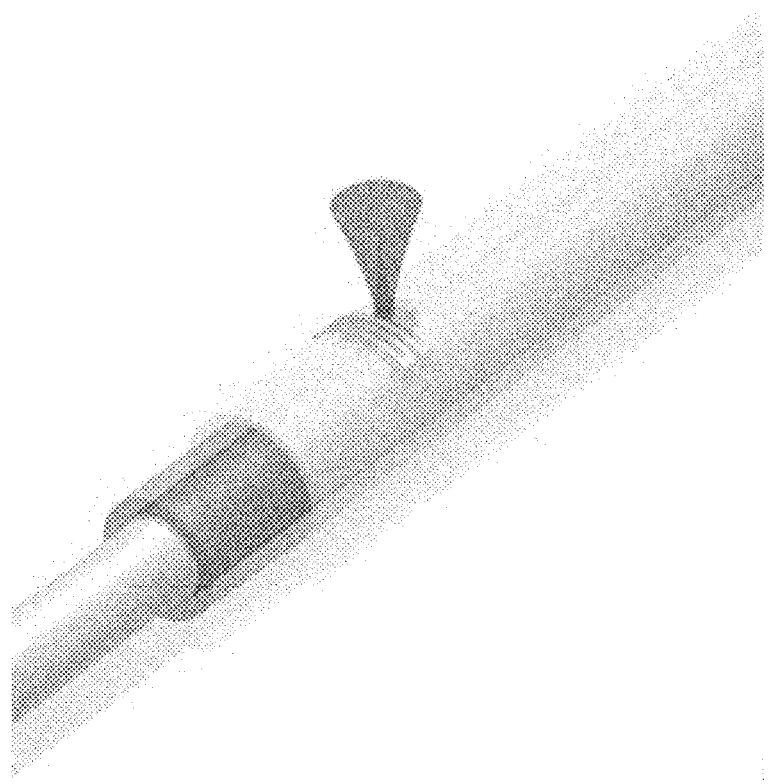
Figure 8C:
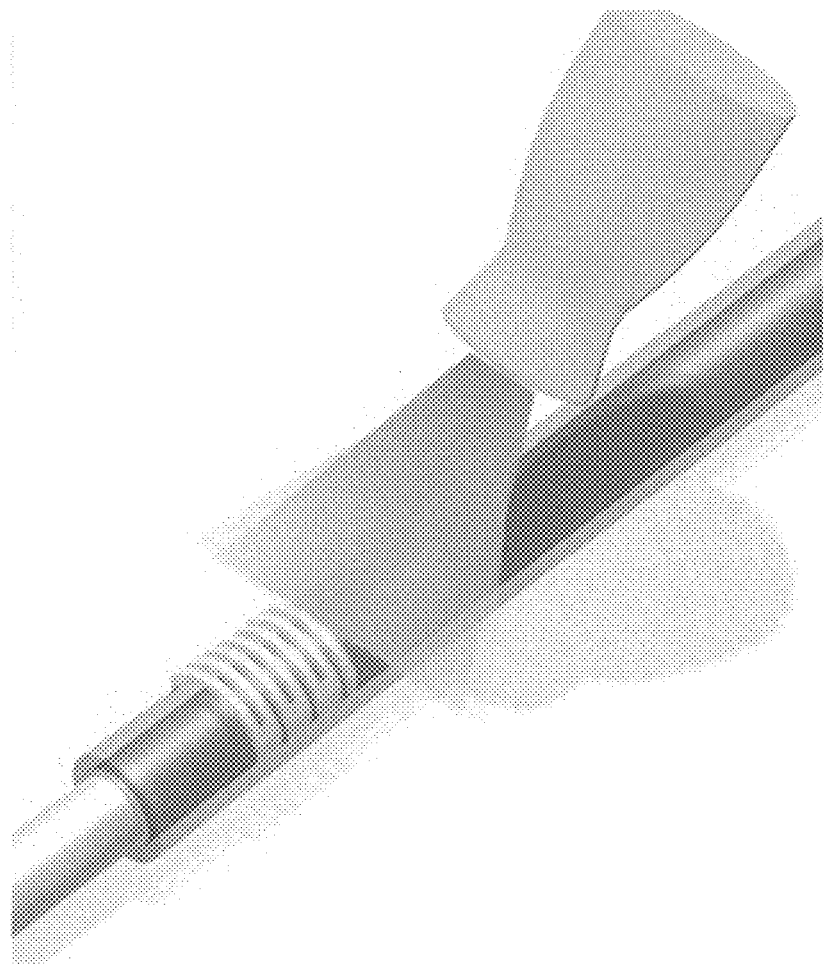

FIGS. 8a to 8c illustrate a procedure of forming a micro-pattern on a surface of a wire in accordance with an example method of the present invention.

In step of FIG. 8a, the wire is immersed in the nanoparticle solution and then is slowly taken out, so that a nanoparticle solution layer is applied to the surface of the wire. At this time, the wire is taken out at a constant speed so that the nanoparticle solution layer is formed with a uniform thickness. Further, it is possible to control the thickness of the nanoparticle solution layer to be applied by controlling the speed at which the wire is taken out.

In step of FIG. 8b, a micro-pattern is formed by irradiating the nanoparticle solution layer coated on the surface of the wire with a Bessel beam. Before step (b), a step of fixing both ends of the wire may be performed.

In step of FIG. 8c, once the formation of the micro-pattern on the surface of the wire by laser irradiation is finished, a step of removing residues such as a nanoparticle solution may be performed to complete the production of a wire having the micro-pattern formed thereon.

Hereinafter, an example apparatus for performing a method for forming a micro-pattern on a surface of a wire in accordance with the present invention will be described.

Since the micro-pattern formed by the process of the present invention has a resolution on a level of 1 μm, it is very important to control the position of the wire in order to form the micro-pattern on the surface of the wire. To this end, it is possible to use an apparatus capable of fixing both ends of the wire while keeping the tension thereof constant, and moving the wire to a desired position or moving the focal point of the laser beam.

Figure 9:
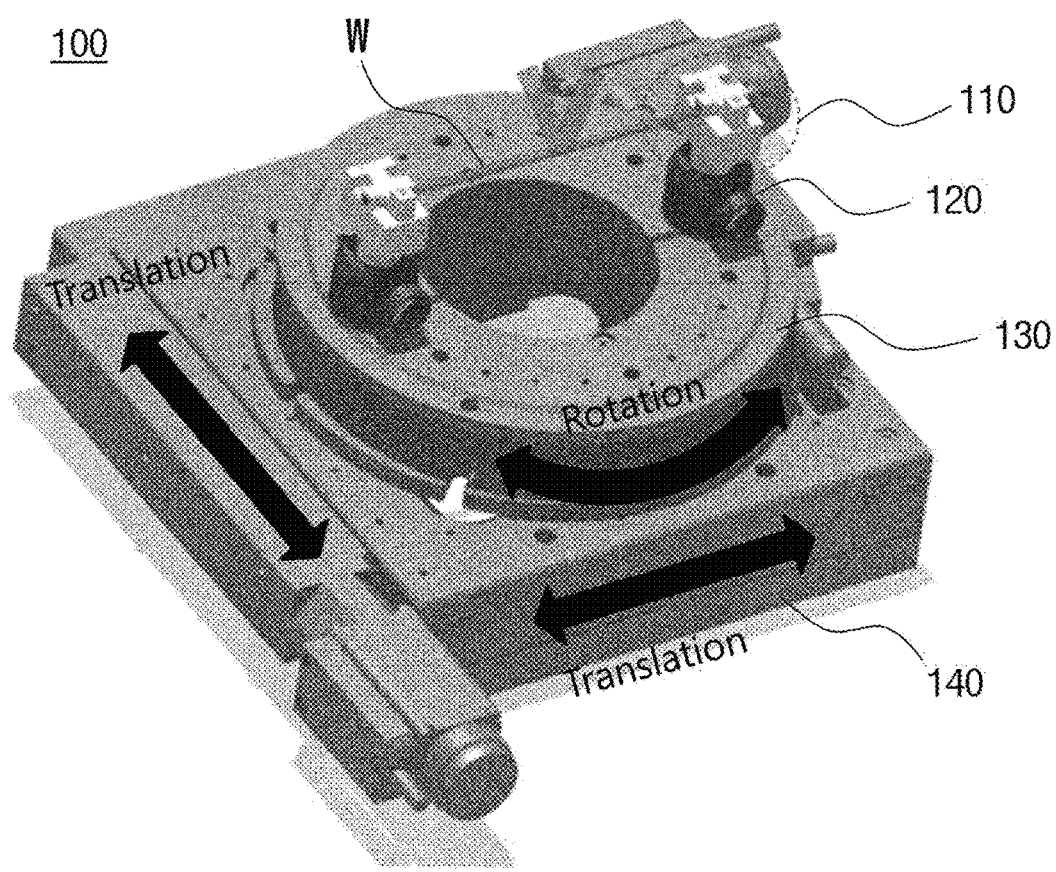
FIG. 9 shows a wire moving device 100 in accordance with an exemplary embodiment of the present invention.

An example wire moving device 100 of the present invention is illustrated in FIG. 9.

The wire moving device 100 comprises a wire mounting member 110 capable of fixing both ends of the wire, a tension retention member 120 configured to pull both ends of the wire with a constant force so that the wire maintains a constant tension, a rotary stage 130 configured to rotate the alignment direction of the wire, and an x-y stage 140 configured to move the wire in the x-axis and y-axis directions.

If the wire moving device 100 is used, the focal point of the laser beam is fixed and the rotary stage 130 and the x-y stage 140 of the wire moving device 100 are operated, so that the focal point of the laser may be positioned at the position where the micro-pattern of the wire is to be formed.

Figure 10:
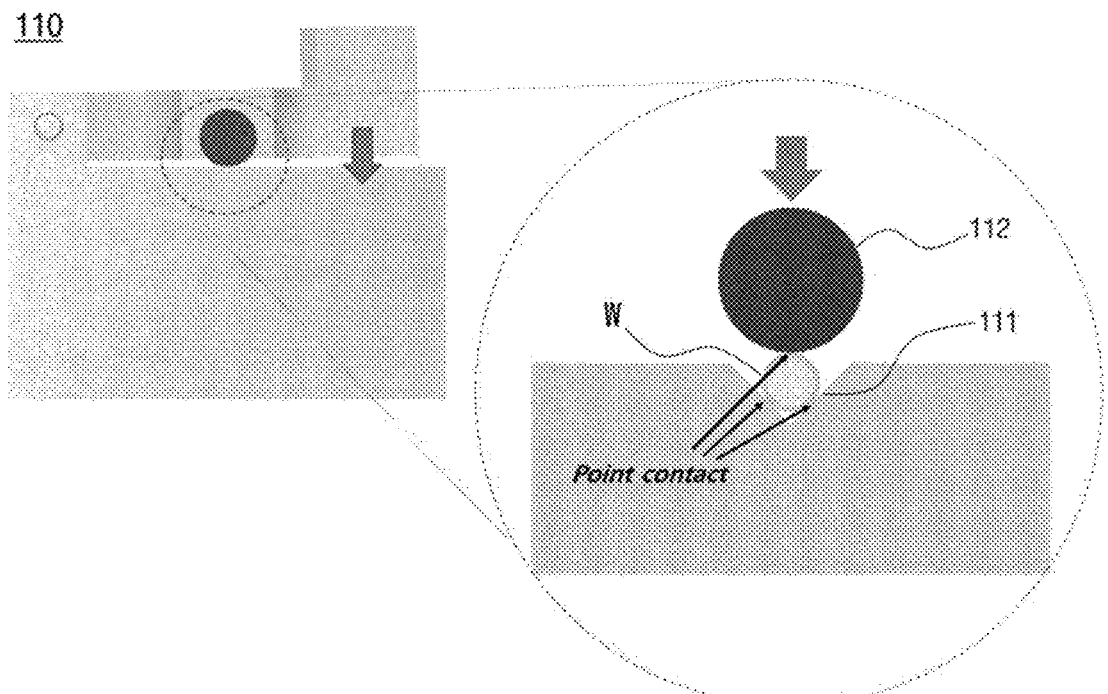
FIG. 10 shows a wire mounting member 110 in accordance with an exemplary embodiment of the present invention.

FIG. 10 is a detailed illustration of the configuration of an example wire mounting member 110 of the present invention.

The wire mounting member 110 may comprise a V-shaped groove 111 configured to contact and fix the lower portion of the wire at two points, and a press-fixing unit 112 configured to contact and fix the upper portion of the wire at one point. The "upper portion" and "lower portion" of the wire are by the concept divided into upper and lower parts based on the cross-section of the wire.

The V-shaped groove 111 preferably has an angle of 90° or more, to facilitate contact with the press-fixing unit 112 above while contacting respectively at the lower two points when the wire is located inside.

In addition, the press-fixing unit 112 may press the upper portion of the wire by, for example, a magnetic force, or the like, so that the wire is firmly fixed to the wire mounting member 110. The press-fixing unit 112 is preferably made of an elastic material such as rubber for a firm fixation while preventing damage to the wire.

However, the wire mounting member 110 is illustrative, and may further be modified or changed within a scope that enables a function of firmly fixing both ends of the wire to be performed.

The tension retention member 120 may be located below the wire mounting member 110 so that the wire is fixed while maintaining a constant tension. The tension retention member 120 serves to pull both ends of the wire with a constant force so that minute shaking or movements do not occur in the site for forming the pattern of the wire during laser operation. At this time, the tension is sufficient if the force is at a level that does not allow minute movements to occur without letting the wire be broken.

When the wire is fixed by the wire mounting member 110 and the tension retention member 120, the surface of the wire is moved to the focal position of the laser beam by the rotary stage 130 and the x-y stage 140, and then the surface of the wire may be moved so that a pre-entered micro-pattern may be formed.

In another embodiment of the present invention, a micro-pattern can be formed on the surface of a wire by moving the focal point of the laser beam with the wire fixed.

Figure 11:
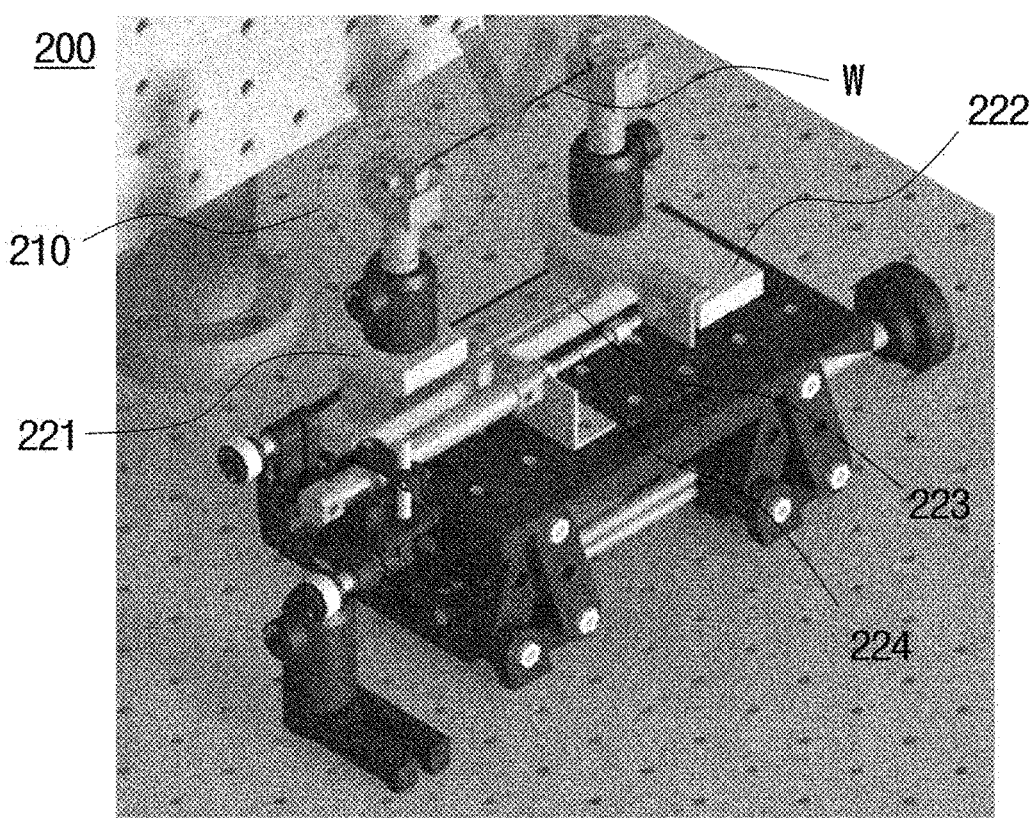
FIG. 11 shows a wire fixing device 200 in accordance with an exemplary embodiment of the present invention.

FIG. 11 shows an example wire fixing device 200 of the present invention.

The wire fixing device 200 may be provided with a wire mounting member 210 as described above to firmly fix the wire, and may keep the area for forming the pattern of the wire from shaking by means of the tension retention member 220.

The tension retention member 220 is provided with a fixing block 221 configured to fix one end of the wire mounting member 210 and a mount adapter 222 configured to fix the other end of the wire mounting member 210 and to be movable in the longitudinal direction of the wire. The mount adapter 222 is located on an LM guide 223 and may move in the longitudinal direction of the wire by the pressing of a press cylinder 224.

The press cylinder 224 may press the mount adapter 222 with a force on a level that prevents the area for forming the pattern from shaking without breaking the wire, so that a constant tension is maintained on the wire.

When the wire is firmly fixed using the wire fixing device 200, the Bessel beam optical system provided with the biaxial scanner and the F-theta lens may be used to form a precise micro-pattern on the surface of the wire, as shown in FIG. 4. That is, the wire is always fixed in the same absolute position, and the biaxial scanner can process the micro-pattern by moving along a desired shape by reflecting the x, y, and theta values of the wire.

Figure 12A:
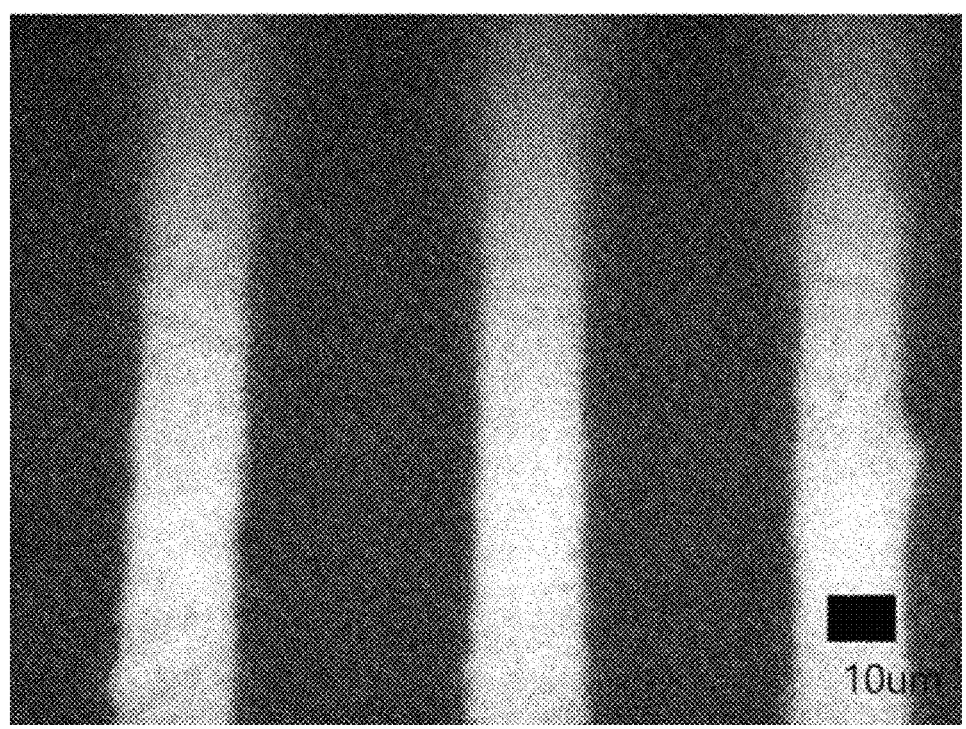
FIGS. 12a and 12b show images of a microelectrode pattern formed on a surface of a wire in accordance with a method of the present invention.
Figure 12B:
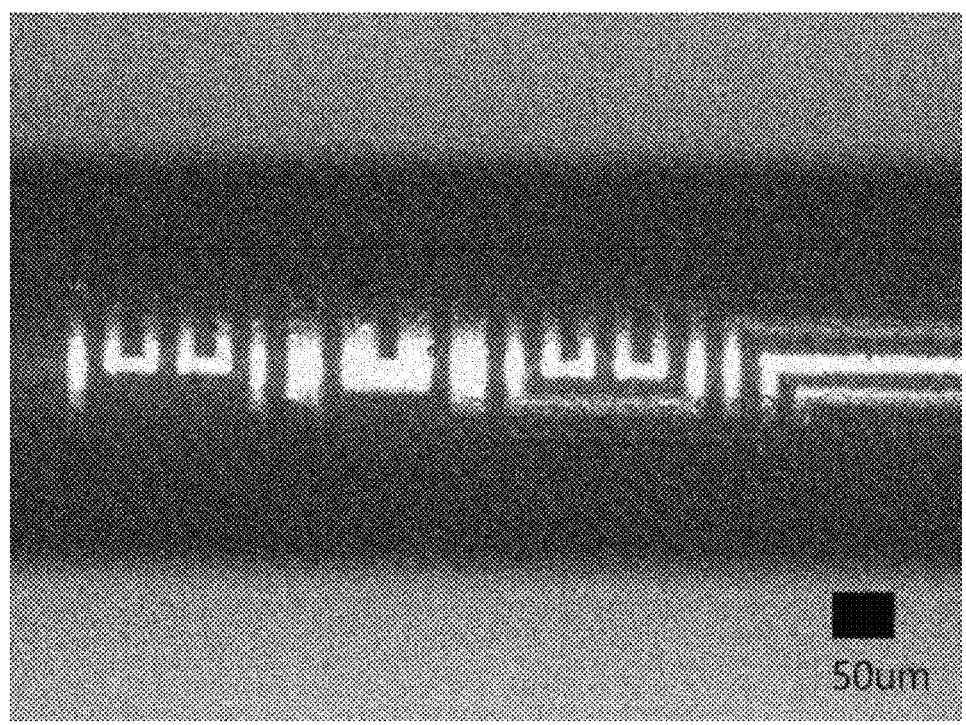

FIGS. 12a and 12b show images of a microelectrode pattern formed on the surface of the wire using the process and apparatus of the present invention. In FIG. 12a, it can be confirmed that a microelectrode pattern having a line width of about 15 μm was formed on the surface of the wire. In addition, it can be confirmed from FIG. 12b that a micro-pattern having a complex shape with various line widths can be formed on the surface of the wire.

According to the process of the present invention, since it is possible to form a micro-pattern on a scale of several to tens of micrometers on the surface of a micro-wire having a diameter on a scale of tens to hundreds of micrometers, it has a high utilization possibility as wires of special applications that are to be inserted into very small places such as the inside of blood vessels in the human body. For example, the wire having the microelectrode pattern formed on the surface thereof produced by the method of the present invention can be inserted into a body such as inside a blood vessel and used as a sensor such as a flow rate sensor, a temperature sensor, etc.

Figure 13:
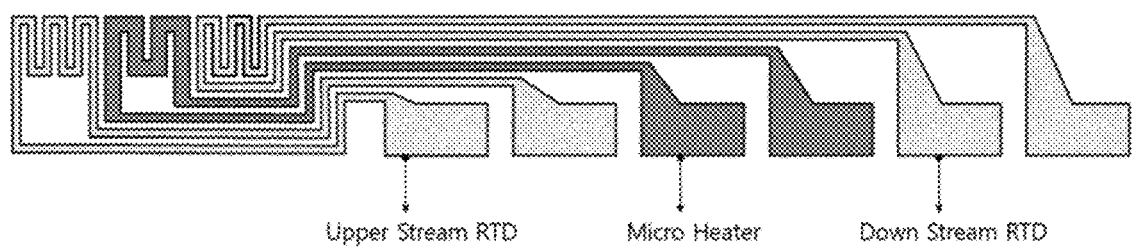
FIG. 13 shows an electrode pattern of an exemplary thermal type flow sensor of the present invention.

FIG. 13 shows an electrode pattern of an exemplary thermal type flow sensor of the present invention. Thermal type flow sensor may be manufactured by coating an insulating layer on the surface of the wire, and then forming resistance temperature detectors (RTDs) in the form of micro patterns on the center heater, the left (upper stream) and right (down stream) of the heater. The size of the sensor may be configured to 0.7 mm in height and 2 to 50 mm in width, but may be set differently according to the purpose of the sensor, and in particular, the length of the width may be adjusted as necessary. Each sensor electrode may have a resistance of 0.8 to 2 kΩ and a thickness of 250 to 300 nm.

Figure 14:
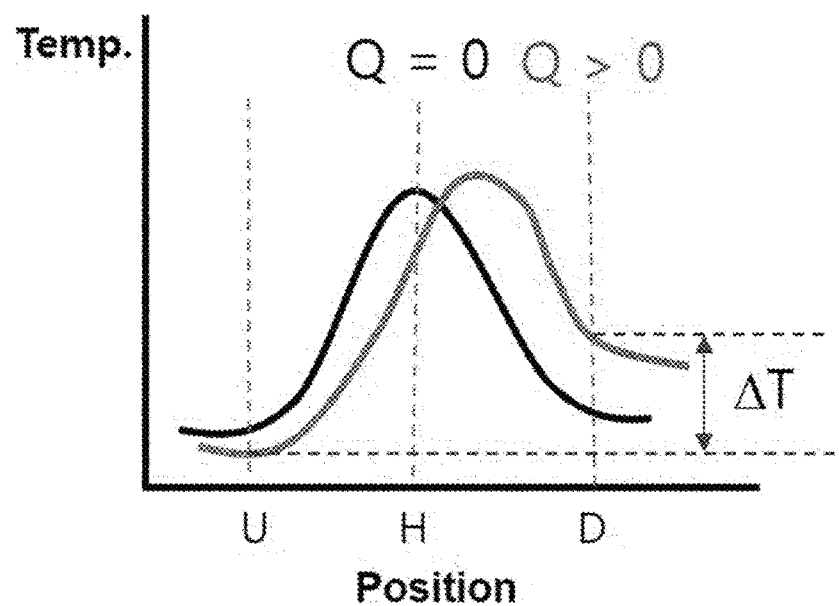
FIG. 14 is a graph showing the operating principle of the thermal flow sensor.

FIG. 14 is a graph showing the operating principle of the thermal flow sensor. In the absence of flow, both resistance temperature detectors maintain thermal equilibrium, and when flow occurs, as the heat from the heater is transmitted to the resistance temperature detector by the flow, the temperature difference between the left and right resistance temperature detectors occurs. It uses the principle of measuring the flow rate by converting the resistance change of the left and right resistance temperature detector due to this temperature difference into a voltage signal by the Wheatstone Bridge Circuit.

In addition, in the present invention, the flow sensor may be patterned in the form of a thermoelectric type flow sensor as well as a thermal type flow sensor. In the case of the thermoelectric type flow sensor, the center heater is patterned by the process of the present invention while the insulating layer is coated on the surface of the wire, and then another insulating layer is coated on the center heater layer. Thereafter, the left and right temperature sensor regions of the heater may be patterned using two types of metallic inks having different Seebeck constants in the form of a thermopile in which several thermocouples are connected. When flow occurs, the flow rate may be calculated by directly measuring the voltage due to the temperature difference generated through the thermoelectric effect in the left and right regions of the center heater.

Moreover, it can be used not only as medical wires that require a micro-diameter but also as construction wires with a large diameter, and since it can be readily applied to wires of various materials, shapes, and uses, it has a very high utilization possibility to be used in all applications requiring metal/non-metal micro-patterns on the surface of a wire.

From the above description, those skilled in the art to which the present invention pertains will understand that the present invention can be implemented in other specific forms without changing the spirit or essential features thereof. In this regard, the embodiments described above should be understood as illustrative in all respects and non-limiting. The scope of the present invention should be construed that all changes or modifications derived from the meaning and scope of the claims to be described later rather than the above detailed description and equivalent concepts are included in the scope of the present invention.

DESCRIPTION OF REFERENCE NUMERALS AND SYMBOLS

100: Wire moving device
110: Wire mounting member
111: V-shaped groove
112: Press-fixing unit
120: Tension retention member
130: Rotary stage
140: x-y stage
200: Wire fixing device
210: Wire mounting member
220: Tension retention member
221: Fixing block
222: Mount adapter
223: LM guide
224: Press cylinder
W: Wire

What is claimed is:

1. A method for forming a micro-pattern on a surface of a wire, comprising:
   a step of applying a nanoparticle solution to the wire to form a nanoparticle solution layer on the surface of the wire;
   a step of irradiating the nanoparticle solution layer with a Bessel beam laser to induce sintering of nanoparticles of the nanoparticle solution layer, thereby forming a micro-pattern on the surface of the wire,
   a step of rotating the wire so that an area having no micro-pattern formed on the wire is positioned at a focal point of the Bessel beam laser; and
   a step of irradiating the nanoparticle solution layer of the area with the Bessel beam laser to induce sintering of the nanoparticles, thereby forming a micro-pattern on the surface of the wire.

2. The method for forming a micro-pattern on a surface of a wire of claim 1, further comprising:

a step of fixing both ends of the wire, before the step of applying the nanoparticle solution to the wire.

3. The method for forming a micro-pattern on a surface of a wire of claim 2, wherein application of the nanoparticle solution is performed by dip coating.

4. The method for forming a micro-pattern on a surface of a wire of claim 2, wherein the fixing the wire is performed by pulling both ends so that a constant tension is maintained on the wire.

5. The method for forming a micro-pattern on a surface of a wire of claim 1, further comprising:
a step of fixing both ends of the wire, after the step of applying the nanoparticle solution to the wire.

6. The method for forming a micro-pattern on a surface of a wire of claim 5, wherein application of the nanoparticle solution is performed by spray coating or inkjet coating.

7. The method for forming a micro-pattern on a surface of a wire of claim 5, wherein the fixing the wire is performed by pulling both ends so that a constant tension is maintained on the wire.

8. The method for forming a micro-pattern on a surface of a wire of claim 1, further comprising:
the step of rotating the wire so that an area having no micro-pattern formed on the wire is positioned at a focal point of the Bessel beam laser; and
the step of irradiating the nanoparticle solution layer of the area with the Bessel beam laser to induce sintering of the nanoparticles, thereby forming a micro-pattern on the surface of the wire.

9. The method for forming a micro-pattern on a surface of a wire of claim 1, further comprising:
a step of removing a residual nanoparticle solution, after the step of irradiating the nanoparticle solution layer with the Bessel beam laser.

10. The method for forming a micro-pattern on a surface of a wire of claim 1, wherein the wire has a diameter of 1 μm to 10 mm.

11. The method for forming a micro-pattern on a surface of a wire of claim 1, wherein the nanoparticle solution has a content of nanoparticles of 5 to 35% by weight.

12. The method for forming a micro-pattern on a surface of a wire of claim 1, wherein the nanoparticle solution has a viscosity of 10 to 200 cP.

13. The method for forming a micro-pattern on a surface of a wire of claim 1, wherein the nanoparticles are one or more selected from a group consisting of copper (Cu), aluminum (Al), chromium (Cr), nickel (Ni), gold (Au), silver (Ag), cobalt (Co), iron (Fe), palladium (Pd), platinum (Pt), titanium (Ti), zinc (Zn) and silica.

14. The method for forming a micro-pattern on a surface of a wire of claim 1, wherein the nanoparticle solution layer is applied with a thickness of 10 nm to 1 mm to the surface of the wire.

15. The method for forming a micro-pattern on a surface of a wire of claim 1, wherein, with a position of the wire fixed, a focal point of the Bessel beam laser is moved to irradiate a predetermined area of the nanoparticle solution layer with the laser.

16. The method for forming a micro-pattern on a surface of a wire of claim 1, wherein, with a position of the focal point of the Bessel beam laser fixed, a position of the wire is moved to irradiate a predetermined area of the nanoparticle solution layer with the laser.

17. The method for forming a micro-pattern on a surface of a wire of claim 1, wherein the laser has a power of 1 to 10 W.

* * * * *